(12) United States Patent
Mrue

(10) Patent No.: US 8,338,371 B2
(45) Date of Patent: Dec. 25, 2012

(54) ACCELERATED ANGIOGENESIS-INDUCING PROTEIN, COMPOSITIONS INDUCING ACCELERATED ANGIOGENESIS AND USES THEREOF

(75) Inventor: Fatima Mrue, Goiânia-Go (BR)

(73) Assignee: Pelenova Biotecnologia S.A., Terenos-MS (BR)

( * ) Notice: Subject to any disclaimer, the term of this patent is extended or adjusted under 35 U.S.C. 154(b) by 1084 days.

(21) Appl. No.: 12/094,931

(22) PCT Filed: Nov. 24, 2006

(86) PCT No.: PCT/BR2006/000253
§ 371 (c)(1),
(2), (4) Date: Aug. 28, 2008

(87) PCT Pub. No.: WO2007/059597
PCT Pub. Date: May 31, 2007

(65) Prior Publication Data
US 2009/0093404 A1    Apr. 9, 2009

(30) Foreign Application Priority Data
Nov. 24, 2005 (BR) ..................................... 0506041

(51) Int. Cl.
*A61K 38/16* (2006.01)
(52) U.S. Cl. .......................................... 514/7.7; 530/370
(58) Field of Classification Search .................... None
See application file for complete search history.

(56) References Cited

U.S. PATENT DOCUMENTS

| 5,457,093 A | 10/1995 | Cini et al. |
| 6,589,544 B2 * | 7/2003 | Leong ............................ 424/402 |
| 6,759,517 B1 | 7/2004 | Cardosa et al. |
| 2004/0171812 A1 | 9/2004 | Mad Arif et al. |

OTHER PUBLICATIONS

Miles, A. A., et al., "Vascular Reacions to Histamine, Histmine-Liberator and Leukotaxine in the Skin of Guinea-Pigs", J. Physiol. (1952), 118, pp. 228-257.
Wilting, Jorg., et al., "A Modified Chorioallantoic Membrane (CAM) Assay for Qualitative and Quantitative Study of Growth Factors", Anat Ernbroyl (1991) 183, pp. 259-271.
International Preliminary Report on Patentability with Written Opinion, International Patent Application No. PCT/BR2006/000253, date of issuance May 27, 2008, 5 pages.
International Preliminary Report on Patentability with Written Opinion, International Patent Application No. PCT/BR2009/000185, date of issuance Jan. 5, 2011, 4 pages (corresponds to U.S. Appl. No. 13/001,288).
International Search Report, International Patent Application No. PCT/BR2009/000185, date of actual completion of the search Sep. 22, 2009, 4 pages (corresponds to U.S. Appl. No. 13/001,288).
Bradley et al., "Measurement of Cutaneous Inflammation: Estimation of Neutrophil Content With an Enzyme Marker." The Journal of Investigative Dermatology, 1982, vol. 78, pp. 206-209.
Cheng et al., "Matrine Improves 2, 4, 6-trinitrobenzene Sulfonic Acid-Induced Colitis in Mice." Pharmacological Research, 2006, vol. 53, pp. 202-208.
Fiocchi, "Inflammatory Bowel Disease: Etiology and Pathogenesis." Gastroenterology, 1998, vol. 115, pp. 182-205.
Hartree, "Determination of Protein: A Modification of the Lowry Method that Gives a Linear Photometric Response." Analytical Biochemistry, 1972, vol. 48, pp. 422-427.
Lowry et al., "Protein Measurement With the Folin Phenol Reagent." Biological Chemistry, 1951, vol. 193, pp. 265-275.
Neurath et al., "Antibodies to Interleukin 12 Abrogate Established Experimental Colitis in Mice." The Journal of Experimental Medicine, Nov. 1995, vol. 182, pp. 1281-1290.
Rogerio et al., "Anti-Asthmatic Potential of a D-galactose-binding Lectin From Synadenium Carinatum Latex." Glycobiology, 2007, vol. 17, No. 8, pp. 795-804.
Wititsuwannakul et al., "A Lectin From the Bark of the Rubber Tree (*Hevea brasiliensis*)." Phytochemistry, 1998, vol. 47, No. 2, pp. 183-187.

* cited by examiner

Primary Examiner — Christopher R. Tate
Assistant Examiner — Roy Teller
(74) Attorney, Agent, or Firm — Fitch, Even, Tabin & Flannery, LLP

(57) ABSTRACT

The present invention refers to an angiogenesis-inducing protein, a composition containing it and the uses of said protein.

9 Claims, 4 Drawing Sheets

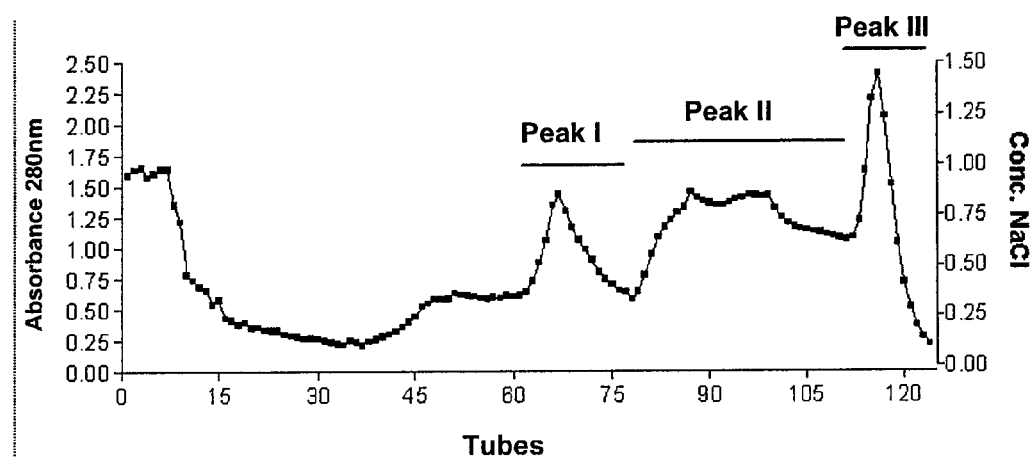
Figure 1 – Natural latex chromatography in DEAE-cellulose

Figure 2 – Reverse phase HPLC Chromatography of the fraction of peak I
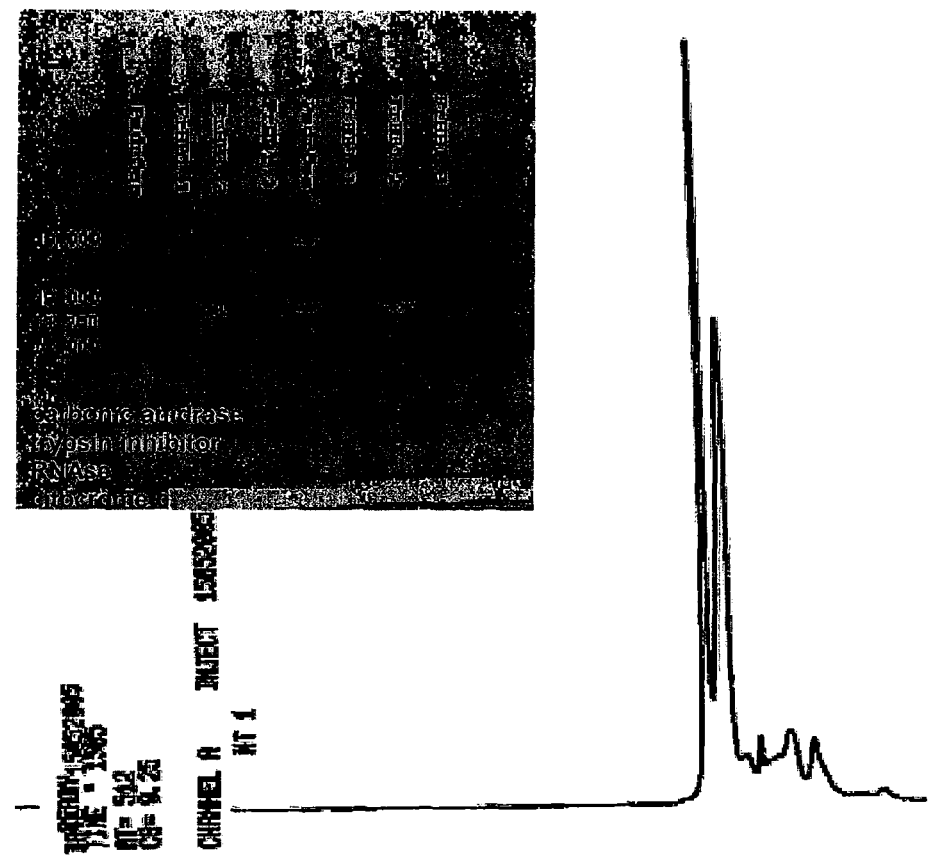

Figure 3 – Activity of increasing vascular permeability of peaks I, II and III
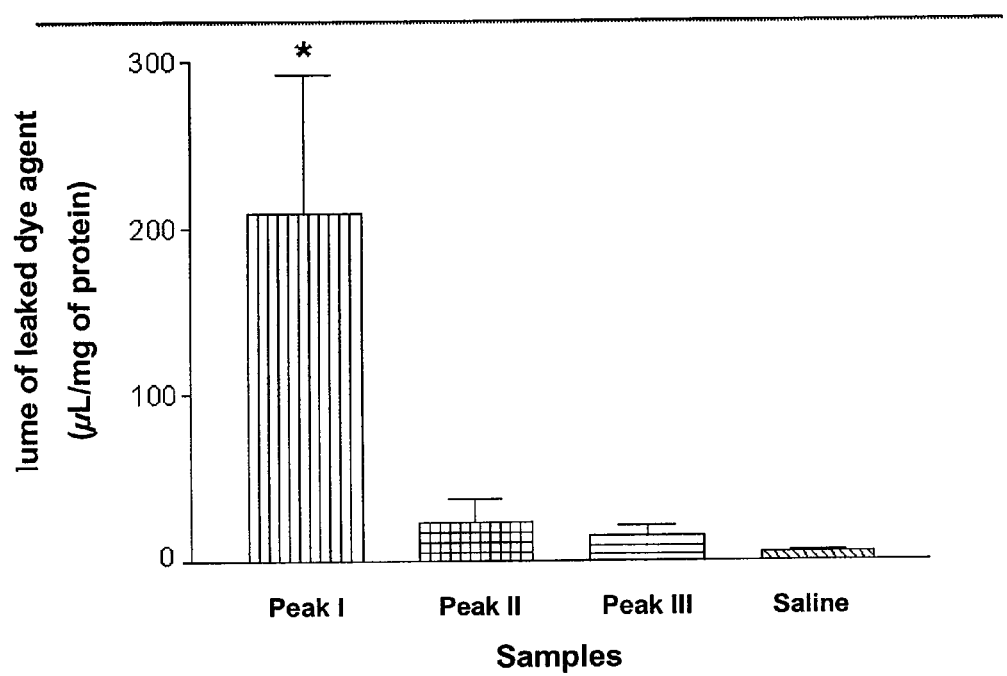

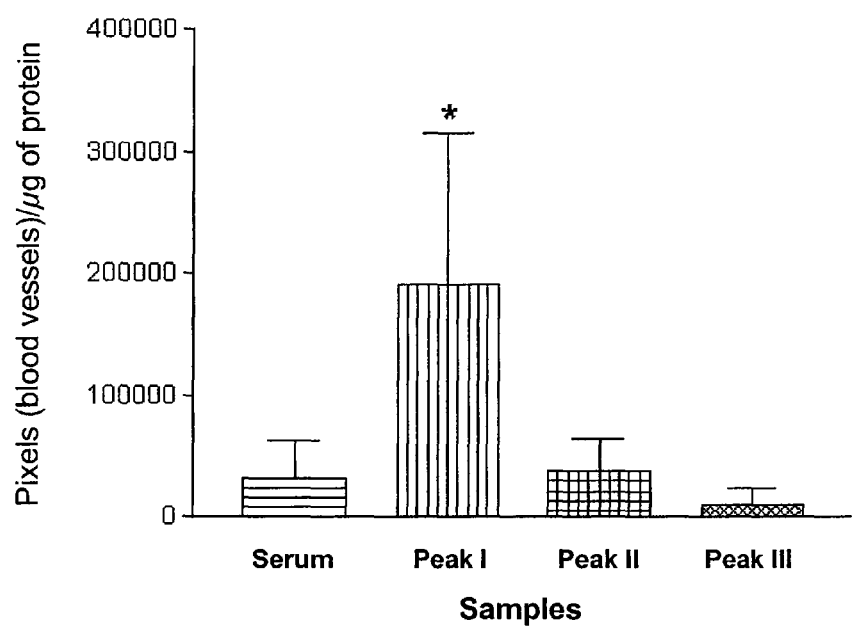
Figure 4 – Relative quantification of blood vessels on CAM images (use of Softwares GIMP and ImajeJ)

ACCELERATED ANGIOGENESIS-INDUCING PROTEIN, COMPOSITIONS INDUCING ACCELERATED ANGIOGENESIS AND USES THEREOF

CROSS-REFERENCE TO RELATED APPLICATIONS

This application is a §371 National Phase application of International Application PCT/BR06/000253 filed on Nov. 24, 2006, claiming priority to Brazilian patent application No. PI 0506041-9, filed on Nov. 24, 2005, both of which are hereby incorporated herein by reference in their entirety.

FIELD OF THE INVENTION

The present invention refers to an angiogenesis-inducing protein, meaning that it induces accelerated cicatrisation and/or revascularization of affected animal tissue, as well as compositions containing it, and uses for it. It is useful, for instance, in the fields of human and animal medicine and odontology, and cosmetics.

BACKGROUND OF THE INVENTION

Angiogenesis is a complex biological process that favors the formation of new capillaries from pre-existing vasculature. It occurs in many physiological and pathological conditions and is controlled by the net balance between molecules having negative and positive regulatory activities. From the point of view of medical applications, cicatrisation many times involves angiogenesis in the reconstitution of damaged or otherwise affected regions requiring revascularization, e.g. diabetic feet injuries or injuries caused by accidents.

Various products intended to cicatrize by inducing angiogenesis are known, but up to now they are extremely expensive, such as growth factors derived from recombinant human platelets, such as mentioned by the U.S. Pat. No. 5,457,093.

Another aspect of the invention is the use of the protein of the invention in the formulation of products able to stimulate the formation of new blood vessels in the dermis (angiogenesis), improving local irrigation and, consequently, the perfusion of nutrients and oxygen to the skin, with stimulus to the production of collagen, elastic fibers and glycosaminoglycans, rejuvenation and/or retarding ageing of that skin, as well as eliminating or decreasing the formation or wrinkles, lines of expression and liver spots, in normal or aged skin.

With the formation of new capillaries along with the improvement of the blood irrigation, the angiogenesis makes the invention useful in bandages, prosthesis, medical, dermatological and cosmetic products, among others.

DESCRIPTION OF THE INVENTION

The inventors found out in their research that a given vegetal protein from the latex of certain plants induces accelerated angiogenesis in animal tissue. Examples of such lactiferous plants are Euphorbiaceae, for instance rubber tree (*Hevea brasiliensis*), Apocinaceae, for instance mangaba tree (*Hancornia speciosa* Gomes) and rowan tree (*Sorbus aucuparia*), Compositae, for instance guayule (*Parthenium argentatum*), Caricaceae, for instance papaya tree (*Carica papaya*), which are easily and widely available, therefore with associated low cost.

It is an acid dimeric protein, with molecular weight of about 20 kDa, each subunit with molecular weight of approximately 10 kDa, linked by disulfide bridges, isoelectric point of about 4.25, soluble in water solutions, stable at pH 3 to 10 at temperatures of up to about 75° C. Its action over affected tissue is to provide accelerated cicatrisation or revascularization, efficiently helping the process provided by the body. That protein is also useful by itself, or in the composition of products, aimed at rejuvenation and whitening the skin, reducing wrinkles and lines of expression, removing liver spots, for making prosthesis for internal use, and general use in medicine and odontology where angiogenesis plays an important role.

Without imposing any limitation to the invention, it is believed that each sub-unit of the dimeric protein of the invention is the isoform of a same protein of about 100 aminoacids.

A particular source for the protein of the invention is the *Hevea brasiliensis* latex, but it may also be obtained synthetically, with no connection to a vegetal origin.

The person skilled in the art would not be induced to research the issue, since the allergic reaction to latex presented by part of the population has been long known, especially related to the use of surgical gloves and sexual preservatives.

Once synthesized or purified from its natural source, the protein of the invention is used as such or under any appropriate pharmaceutical form (topical or systemic), internally or externally to the animal body, particularly the human body. That includes, without excluding any other form, creams, pastes, ointments, salves, lotions, dispersions, emulsions, solutions, powders, sprays, injectable liquids, pellets, tablets, bolus, etc. with immediate or controlled release. The person skilled in the art knows how to formulate such products with appropriate excipients and carriers to the aimed administration—an example of such knowledge is set in the publication "Remington: The Science and Practice of Pharmacy", 19th ed., ed. A. R. Gennaro A R., 1995, Mack Publishing Company, Easton, Pa., USA.

Cosmetic compositions are also manufactured using the protein of the invention. The use of the protein of the invention in implants of skin is also an aspect of the invention.

In another aspect, the invention contemplates uses of said protein in the reconstruction of parts or walls of internal bodies, e.g. by direct application of the protein to said organs or combined with structural material, e.g. polymeric (such as natural latex film or another appropriate synthetic polymer), by full or partial substitution of organs, e.g. by prosthesis implantation. Odontological prosthesis are also encompassed by the invention.

Within another embodiment of the invention, not excluding any other, the protein of the invention is used in applications providing cosmetic effects, that is, benefiting the user even when not exposed to morbid conditions, diseases or organic dysfunctions causing wounds or disrupture of the animal tissue (especially skin, walls of organs, bone or mucosa). In this sense, the invention concerns the use of the protein revealed herein to heal tissue cuts, bruises or tissue trauma (scraping, perforation, etc.) caused by plastic surgeries, e.g. to remove flaccid skin, wrinkles, gills, nevus or warts, besides topical products for rejuvenation, gingival correction, skin abrasion (peeling), excessive exposure to sun radiation, recently tattooed skin, recovery of hair implantation, aesthetical cuts in ears or tails of dogs, etc.

Without being bound by theory, it is believed that the protein of the invention, once applied onto the skin, penetrate the epidermis, effecting an intradermal transport through the micelles, leading the active principle, which brings about the angiogenic factor and stimulates the formation of new blood vessels in the dermis, increasing the perfusion and consequently improving the nutrition and oxygenation of the skin layers. Fibroblasts are then stimulated to proliferated and improve the production of substances of extracellular matrix, such as collagens, elastic fibers and glycosaminoglycans. Simultaneously, fibroblasts are induced to liberate the metaloproteinases, that act as collagens, elastine and the proteins with crossed links, partly responsible for skin elasticity loss.

The examples that follow show, in a merely illustrative way, a few particular aspects of the invention, not however limiting it in any way. The limitations of the invention, as well known, are established in the attached claims.

BRIEF DESCRIPTION OF THE DRAWINGS

FIG. 1 shows natural latex chromatography in DEAE-cellulose;

FIG. 2 shows reverse phase HPLC chromatography of the fraction of peak I;

FIG. 3 shows activity of increasing vascular permeability of peaks I, II and III; and FIG. 4 shows relative quantification of blood vessels on CAM images with use of Softwares GIMP and ImajeJ.

EXAMPLES

1. Obtaining the Angiogenesis-inducing Protein

Fresh natural latex of *Hevea brasiliensis* was coagulated and centrifuged, so as to obtain a lower solid fraction and serum, that is, a supernatant aqueous fraction.

Said serum was submitted to chromatographic ion exchange separation in a diethylaminoethyl cellulose (DEAE-cellulose) column. Washings were performed with NaCl and absorbance (optical density), of the taken tubes was measured at 280 nm. Three main peaks were identified, as can be seen in the attached FIG. 1.

In reverse phase HPLC chromatography (high performance liquid chromatography), as shown in FIG. 2, a sample of the fraction of peak I revealed the presence of the dimeric protein of the invention—two subunits—with total molecular weight of about 20 kDa, soluble in water solutions and stable in pH 3 to 10 at temperatures of up to about 75° C.

2. Indirect Verification of the Effect of the Protein of the Invention

The generation of new blood vessels is accompanied in almost every state by higher vascular permeability. Therefore, samples of the fractions of the three previously mentioned peaks were evaluated concerning the increase in vascular permeability, with in vivo assays as per Miles, A. A.; Miles, E. E., *J. Physiol.* 118, 228 (1952). The result revealed more intense induction to angiogenesis by the peak I fraction, by the higher volume of leaked dye agent than for the other peaks—that is, indicating higher presence of angiogenesis inductor in the fraction of peak I.

3. Direct Verification of the Effect of the Protein of the Invention

By following the methodology of Wilting, J. et al, *Anat. Embryol.* 186, 251 (1991), the angiogenic activity on the chorio-allanthoic membrane (CAM) of hen embryos was determined. Applications were made with the fractions corresponding to peaks I, II and III, as well as with a control of physiological serum, taking photos of the result. Images obtained were treated with the softwares GIMP (GNU Image Manipulation Program) and ImajeJ Q (from the National Institutes of Health, Bethesda, Md., USA) for the relative quantification of blood vessels. FIG. 4 shows that the peak I fraction was the one causing the largest appearance of vessels.

The teachings presented herein, as well as the examples and graphs, allow the person skilled in the art to work the invention in ways that differ from what was revealed here in, but keeping function and results in the same order of magnitude, therefore not escaping from the scope of protection determined in the attached claims.

The invention claimed is:

1. An isolated accelerated angiogenesis-inducing protein extracted from latex of *Hevea brasiliensis*, the protein consisting of an acid dimeric protein having a molecular weight of about 20 kDa, the dimeric protein comprising two subunits linked by disulfide bridge, each subunit comprising about 100 amino acids, and each subunit having a molecular weight of about 10 kDa, wherein the protein is soluble in water solutions, and stable in pH from 3 to 10 at temperatures of up to about 75° C.

2. An accelerated angiogenesis-inducing composition comprising the protein of claim 1.

3. A composition for cicatrisation of animal body tissue, comprising the accelerated angiogenesis-inducing protein of claim 1.

4. A material for building, reconstructing or substituting parts and walls of internal organs and for vascular repair, comprising the accelerated angiogenesis-inducing protein of claim 1.

5. The material according to claim 4, further comprising a polymeric structural material selected from a group consisting of natural latex film and synthetic polymer.

6. A material for manufacturing prosthesis for full or partial substitution of organs in an animal body, comprising the material of claim 5.

7. A product for cosmetic application, comprising the accelerated angiogenesis-inducing protein of claim 1.

8. The isolated accelerated angiogenesis-inducing protein of claim 1, wherein the protein is isolated by a method comprising:
    treating latex of *Hevea brasiliensis* to coagulate the latex;
    centrifuge the coagulated latex to obtain a solid fraction and a supernatant fraction;
    treating the supernatant fraction with chromatographic ion exchange separation in a diethylaminoethyl cellulose column;
    washing the column with an alkali metal salt;
    measuring absorbance with UV light at a wavelength of 280 nm; and
    isolating the protein corresponding to peak I shown in FIG. 1.

9. The isolated accelerated angiogenesis-inducing protein of claim 8, wherein the alkali metal salt is sodium chloride.

* * * * *